(12) United States Patent
Hamamoto et al.

(10) Patent No.: US 7,087,238 B2
(45) Date of Patent: Aug. 8, 2006

(54) SHEET-LIKE PACKS

(75) Inventors: Hidetoshi Hamamoto, Tokushima-ken (JP); Yasuko Abe, Kagawa-ken (JP); Sven H. Gohla, Hamburg (DE); Heiner Max, Hamburg (DE); Thorsten Cassier, Hamburg (DE)

(73) Assignees: Teikoku Seiyaku Co., LTD, Kagawa-ken (JP); Beirsdorf Aktiengesellschaft, Hamburg (DE)

( * ) Notice: Subject to any disclaimer, the term of this patent is extended or adjusted under 35 U.S.C. 154(b) by 39 days.

(21) Appl. No.: 10/168,374

(22) PCT Filed: Nov. 7, 2001

(86) PCT No.: PCT/JP01/09715

§ 371 (c)(1),
(2), (4) Date: Jun. 20, 2002

(87) PCT Pub. No.: WO02/38111

PCT Pub. Date: May 16, 2002

(65) Prior Publication Data

US 2003/0049306 A1   Mar. 13, 2003

(30) Foreign Application Priority Data

Nov. 7, 2001   (JP) ............................. 2000-341834

(51) Int. Cl.
*A61K 6/00* (2006.01)
*A61K 31/74* (2006.01)
*A61F 13/00* (2006.01)

(52) U.S. Cl. ...................... 424/401; 424/443; 424/449; 424/78.03; 424/78.02; 514/844; 514/944

(58) Field of Classification Search ................ 424/400, 424/401, 443, 445, 447, 448, 449, 484, 488, 424/78.02, 78.03, 94.1; 514/678, 953
See application file for complete search history.

(56) References Cited

U.S. PATENT DOCUMENTS

| | | | |
|---|---|---|---|
| 5,045,553 A * | 9/1991 | Ueda et al. .................. 514/344 |
| 5,378,461 A | 1/1995 | Neigut | |
| 5,456,745 A * | 10/1995 | Roreger et al. .......... 106/140.1 |
| 5,912,272 A | 6/1999 | Hoppe et al. | |
| 6,048,886 A * | 4/2000 | Neigut ........................ 514/412 |
| 6,066,327 A * | 5/2000 | Gubernick et al. ......... 424/401 |
| 6,723,667 B1 | 4/2004 | Saito et al. | |

2003/0113356 A1 * 6/2003 Deckner et al. ............ 424/401

FOREIGN PATENT DOCUMENTS

| | | |
|---|---|---|
| DE | 100 20 874 A1 | 5/2001 |
| DE | 10020874 A | 5/2001 |
| EP | 1 104 670 A1 | 6/2001 |
| EP | 1 147 759 A1 | 10/2001 |
| EP | 1 151 749 A1 | 11/2001 |
| GB | 2 235 204 A | 2/1991 |
| JP | 56-115707 A | 9/1981 |
| JP | 56-115708 A | 9/1981 |
| JP | 57-2213 A | 1/1982 |
| JP | 57-2214 A | 1/1982 |
| JP | 58-180410 | * 10/1983 |
| JP | 58-180410 A | 10/1983 |
| JP | 59-093012 A | 5/1984 |
| JP | 59-93012 A | 5/1984 |
| JP | 62-39512 A | 2/1987 |
| JP | 63-162610 A | 7/1988 |
| JP | 63-183507 A | 7/1988 |
| JP | 1-207217 A | 8/1989 |
| JP | 3-63209 A | 3/1991 |
| JP | 6-279255 A | 10/1994 |
| JP | 08-188527 A | 7/1996 |
| JP | 8-188527 A | 7/1996 |
| JP | 9-241148 A | 9/1997 |
| JP | 10-130162 A | 5/1998 |
| JP | 11-130625 A | 5/1999 |
| JP | 11-228340 A | 8/1999 |
| JP | 2000-063230 A | 2/2000 |
| JP | 2000-63230 A | 2/2000 |
| JP | 11130625 | * 2/2000 |
| WO | WO 94/13235 A1 | 6/1994 |
| WO | WO 00/02526 A1 | 1/2000 |
| WO | WO 01/78678 A1 | 10/2001 |

OTHER PUBLICATIONS

Hashizume, J Dermatol. Aug. 2004;31(8):603-9.*
Nola et al, Acta Dermatovenerol Croat. 2003;11(1):32-40.*
Partial English language translation of Japanese Application No. 11-130625 A (previously submitted with Reply of Aug. 4, 2004).

* cited by examiner

*Primary Examiner*—Sreeni Padmanabhan
*Assistant Examiner*—Sharmila S. Gollamudi
(74) *Attorney, Agent, or Firm*—Birch, Stewart, Kolash & Birch, LLP

(57) ABSTRACT

A sheet-like pack effective for prevention and improvement of small wrinkles on skin, comprising a water soluble high molecular weight compound, water and ubiquinone 10 as an active ingredient, which are contained in a base.

13 Claims, 1 Drawing Sheet

SHEET-LIKE PACKS

This application is the national phase under 35 U.S.C. § 371 of PCT International Application No. PCT/JP01/09715 which has an International filing date of Nov. 7, 2001, which designated the United States of America.

TECHNICAL FIELD

The present invention relates to sheet-like packs excellent in prevention and improvement of small wrinkles on human skin.

BACKGROUND ART

Small wrinkles on skin are not favorable for smooth skin and are very important as an index of skin aging.

As skin is often directly exposed to ultraviolet rays of sunlight, the skin receives more oxidation-stress based on environmental factors than other organs do. The surface of the cell membrane of skin cells (chrotoplast) or the cell membrane of skin-cells contains a large amount of unsaturated fatty acids, and UV-rays advance the oxidation of these fatty acids.

Ultraviolet rays occupy 6% of sunlight. UVB (290 nm–320 nm) especially produces active oxygen on skin like ionizing radiations do. It is said that the active oxygen produces free radicals, and then by mediation thereof produces peroxidized lipids. As a result, it is possible that the cells lead to dysfunction like oxygen deactivation, or cause necrosis of the cells. Such aging of skin-cells appears on the surface of skin (epidermis) and becomes one of the factors that causes small wrinkles (exogenous factor).

In addition, skin is apt to lose water because it is exposed to outside air. The water content of human skin is usually about 60%. When the water content becomes less than 40% upon drying of the skin, the skin loses tension and gloss to cause small wrinkles (endogenous factor).

As ways for preventing small wrinkles, preparations containing the following substances are proposed: peptides having masking activity, such as tri- or tetra-peptide (Japanese Patent Publication A 56-115707), penta-peptide (Japanese Patent Publication A 56-115708) or new peptides (Japanese Patent Publication A 57-2213, Japanese Patent Publication A 57-2214); blood circulation promoters, such as carpronium chloride (Japanese Patent Publication A 62-39512), organic germanium compounds (Japanese Patent Publication A 63-183507) or inorganic germanium compounds (Japanese Patent Publication A 01-207217); humidic reservation agents such as hyaluronic acid (Japanese Patent Publication A 03-63209), and humidic reservation co-agents such as hyaluronidase inhibitors (Japanese Patent Publication A 06-279255, Japanese Patent Publication A 09-241148, Japanese Patent Publication A 10-130162).

However, packs containing the above-mentioned active substances have not accomplished enough effect for the prevention or improvement of keratinization of skin or small wrinkles of skin.

On the other hand, U.S. Pat. No. 5,889,062 discloses use of a combination of ubiquinone 10 or its derivative and a plastoquinone or its derivative for the care of aged skin.

Further, it is reported that in cosmetics, ubiquinone 10 is useful for protection against skin-aging (Japanese Patent Publication A 58-180410).

However, there have not been developed sheet-like packs dissolving the above-mentioned two problems, namely inhibition of oxidation-stress on skin (exogenous factor) and the water supply to skin in which water content decreases (endogenous factor).

DISCLOSURE OF INVENTION (Problems to be Solved)

The present invention provides sheet-like packs that are excellent in prevention and improvement of small wrinkles, which can prevent oxidation stress of skin and can supply water to the skin.

(Means for Solving Problems)

The present inventors have extensively engaged in solving the above problems, and as a result have found that ubiquinone 10 as an active ingredient has an activity that prevents the exogenous factor of small wrinkles, namely oxidation stress, and a base containing a water soluble high molecular weight compound and water has an excellent activity for supplying water to the skin which is poor in water content (endogenous factor), and by combining these activities (findings) to accomplish excellent effect for prevention or improvement small wrinkles on skin.

Water retained in a high molecular weight compound is kept for longer time than water permeated in cloth or unartificial water itself is done. It is considered that in regard to water permeated in cloth or unartificial water, the water on skin remains more than the amount of water supplied to skin and the remained water together with the supplied water evaporates and therefore, the water retained on a water soluble high molecular weight compound absorbs remaining (extra) water through the water soluble high molecular weight compound, and it can supply water only in as much of an amount as water is supplied to skin.

The present inventors consider how the main endogenous factor of small wrinkles decreases water content in skin and by using a base containing a water soluble high molecular weight compound and water have succeeded in preparing excellent sheet-like packs for prevention and improvement of small wrinkles.

(Effect of Invention)

By using the sheet-like packs of this invention it is possible to prevent aging of skin cells based on UV-rays stress of sunlight, and prevent and improve small wrinkles by supplying water to the skin via water in the base.

The present invention relates to a sheet-like pack comprising a water soluble high molecular weight compound, water and ubiquinone 10 as an active ingredient, which are contained in a base.

Ubiquinone 10 is shown in the following structure:

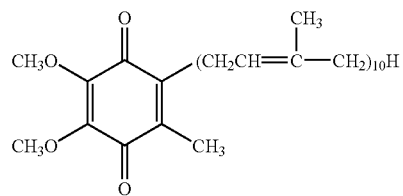

Ubiquinone 10 is called coenzyme 10, Q10, etc., too.

Ubiquinone 10 was extracted and isolated from mitochondria of bovine heart muscle and it was confirmed that ubiquinone 10 is positioned at the electron transfer of myocardial mitochondria and plays an important role in the metabolism of energy. Recently, by applying ubiquinone 10 to human patient (myocardiosis), improvement of myocardial disorder has been observed. As to its mechanism, protection of cells and membrane structure by anti-oxidation activity has been much evaluated. It is cleared that anti-oxidation activity on living body-membrane prevents oxidation-stress of skin-cell membrane by ultraviolet rays (Kurume Doctor's Association Journal, Vol. 49, No. 1, 64–68 1986).

According to the present invention, the amount of ubiquinone 10 is 0.0001–10% by weight per total amount of a base, preferably 0.001–5% by weight. In case of less than 0.0001%, the effect is weakened, and in case of more than 10% the effect is not strengthened, and to use so much ubiquinone is not economical.

Ubiquinone 10 used in the present invention may be one from any origin, but a biotechnologically synthesized one is especially preferable.

The water soluble high molecular weight compounds used in the present invention are illustrated as gelatin, polyacrylic acid or its salt, polyvinylpyrrolidone, carboxyvinyl polymer, sodium carboxymethyl cellulose, hydroxypropyl cellulose, hydroxymethyl cellulose, methyl cellulose, ethyl cellulose, methylvinyl ether-maleic acid anhydride copolymer, starch-sodium acrylate graft polymer, sodium arginate, polyethylene oxide, arabic gum, xanthan gum, tragacanth gum, etc., preferably gelatin, polyacrylic acid or its salt, carboxyvinyl polymer, sodium carboxymethyl cellulose, starch-sodium acrylate graft polymer. The water soluble high molecular weight compound may be used alone or in combination of them.

The content of the water soluble high molecular weight compound is 1–30% by weight per total amount of a base, preferably 3–20% by weight. In the case that the content of the water soluble high molecular weight compound is less than 1%, the base becomes inferior in the formation of sheet-like packs. In the case that the content of the high molecular compound is more than 30%, viscosity of the base increases and efficiency for manufacturing the packs will be down.

Water used in the present invention is purified water, sterilized water, etc. Water is used for the source of supply to skin. The content of water is 30–90% by weight per total amount of a base, preferably 50–70%. In case of less than 30%, water does not fully work as the source of supply of water to the skin and sheet-form preservation unfavorably decreases. On the other hand, in case of more than 90%, viscosity of the base and sheet-form preservation unfavorably decreases.

The sheet-like packs of the present invention are used as cosmetics or quasi-drugs for preventing and improving small wrinkles on skin.

The base used in the present invention may further contain additives used in the usual cosmetics and quasi-drugs, such as fillers, e.g., kaolin, ventonite, titanium oxide; surfactants, e.g., a fatty acid glyceride, polyoxyethylene castor oil, polyoxyethylene hydrogenated castor oil, sorbitan fatty acid ester, polysorbate 80, polysorbate 60, sesquioleic acid sorbitan ester; cross linkers like multivalent metal compound, e.g., dried aluminum hydroxide gel, aluminum glycinate, dihydroxyaluminium amino acetate, synthetic hydrotalcite; wetting agents, e.g., glycerin, sorbitol, propylene glycol, 1,3-butylene glycol, polyethylene glycol; elastic agents, e.g., castor oil, ethanol; coloring agents, e.g., new coccin, tartrazine, brilliant blue FCF, etc.; preservatives, e.g., p-hydroxybenzoate, sorbic acid, isopropylmethylphenol, hinokitiol, phenoxyethanol, etc.

The sheet-like pack of the present invention may contain in the base, a compound having masking activity such as a peptide etc., a circulation promoter, such as carpronium chloride, a germanium compound, etc., a humidic reservation agent such as a hyaluronic acid, etc., or a humidic reservation co-agent such as a hyaluronidase inhibitor, etc., as well as ubiquinone 10.

The content of these active compounds can be decided on the type of preparation.

As a backing used in the packs of the present invention, woven textile, felt or knit etc., which are made of chemical fibers, such as nylon, rayon, polyester or polypropylene, or natural fiber such as cotton, are used. As a cover sheet, plastic film such as polyester film used in the normal plasters is used.

The sheet-like packs of this invention may be in the form of rectangle, ellipse, triangle, boomerang, face mask and so on.

MODE FOR CARRYING OUT THE INVENTION

The present invention is illustrated in detail by examples and experiments as follows, but the invention should not be limited by these examples and experiments. The contents of ingredients in examples and comparative examples present percent by weight.

EXAMPLE

Examples 1–8

According to ingredients indicated in Table 1 and Table 2, sheet-like packs (Examples 1–8) were prepared by the conventional method as follows.

A part of the amount of water soluble high molecular weight compounds and polyvalent alcohols was dissolved in a part of the amount of purified water and to the solution were added other ingredients. The mixture was thoroughly kneaded and ubiquinone 10 and lipophilic compounds were added to the mixture. Thereto, the rest of the water soluble high molecular weight compounds and other ingredients were added and then the mixture was kneaded. Finally, thereto the rest of purified water was added and the mixture was kneaded until it was homologous to give an objective base.

The base thus obtained was extended on a felt and made in a desired form, and packed to prepare objective sheet-like packs.

TABLE 1

| Ingredient | Ex. 1 | Ex. 2 | Ex. 3 | Ex. 4 | Ex. 5 |
|---|---|---|---|---|---|
| Ubiquinone10 | 0.002 | 0.02 | 0.2 | 2 | 0.02 |
| Hyaluronic acid | — | — | — | — | — |
| Polyacrylic acid | 2 | 2 | 2 | 2 | 0.5 |
| Sodium polyacrylate | 5 | 5 | 5 | 5 | 4 |
| CMC sodium | 5 | 5 | 5 | 5 | 3 |
| Geratin | 0.4 | 0.4 | 0.4 | 0.4 | 0.3 |
| Sodium edetate | 0.1 | 0.1 | 0.1 | 0.1 | 0.1 |
| Glycerin | 20 | 20 | 20 | 20 | 15 |
| 70% Sorbitol | 10 | 10 | 10 | 10 | — |
| Dried Al(OH)$_3$ gel | 0.2 | 0.2 | 0.2 | 0.2 | — |
| Synthetic hydrotalcite | — | — | — | — | 0.3 |
| Polysorbate 80 | 0.1 | 0.1 | 0.1 | 0.1 | 0.1 |
| Castor oil | 1 | 1 | 1 | 1 | 1 |
| Glycerin monostearate | — | — | — | — | — |
| Liquid paraffin | — | — | — | — | — |
| Methylparaben | 0.2 | 0.2 | 0.2 | 0.2 | 0.2 |
| Purified water | q.s. | q.s. | q.s. | q.s. | q.s. |
| Total | 100 | 100 | 100 | 100 | 100 |

TABLE 2

| Ingredient | Ex. 6 | Ex. 7 | Ex. 8 | Comp. Ex. 2 | Comp. Ex. 3 |
|---|---|---|---|---|---|
| Ubiquinone 10 | 0.02 | 0.0005 | 7 | — | — |
| Hyaluronic acid | — | — | — | — | 0.5 |
| Polyacrylic acid | 2 | 2.5 | 1.25 | 2 | 2 |
| Sodium polyacrylate | 5 | 6 | 6 | 5 | 5 |
| CMC Na | 5 | 4 | 5.5 | 5 | 5 |
| Geratin | 0.5 | — | 0.5 | 0.4 | 0.4 |
| Sodium edetate | 0.1 | 0.1 | 0.1 | 0.1 | 0.1 |
| Glycerin | 20 | 20 | 20 | 20 | 20 |
| 70% Sorbitol | 30 | 10 | 10 | 10 | 10 |
| Dried Al(OH)$_3$ gel | — | 0.2 | — | 0.2 | 0.2 |
| Synthetic hydrotalcite | 0.2 | — | 0.3 | — | — |
| Polysorbate 80 | 0.1 | 0.1 | — | 0.1 | 0.1 |
| Castor oil | 1 | 1 | — | 1 | 1 |
| Glycerin monostearate | — | — | 2 | — | — |
| Liquid paraffin | — | — | 15 | — | — |
| Methylparaben | 0.2 | 0.2 | 0.2 | 0.2 | 0.2 |
| Purified water | q.s. | q.s. | q.s. | q.s. | q.s. |
| Total | 100 | 100 | 100 | 100 | 100 |

Comparative Example 1

Ingredients indicated in Table 3 were kneaded, and the resulting mixture was immersed onto a hydrophilic felt to prepare sheet-like packs (Comparative example 1).

TABLE 3

| Ingredient | Comparative Example 1 |
|---|---|
| Ubiquinone 10 | 0.002 |
| Glycerin | 20 |
| Polysorbate 80 | 0.1 |
| Methylparaben | 0.2 |
| Purified water | q.s. |
| Total | 100 |

Comparative Example 2

Sheet-like packs (Comparative example 2) were prepared in the same manner as in Example 1 provided that ubiquinone 10 was excluded from the ingredients of Example 1.

Comparative Example 3

Sheet-like packs (Comparative example 3) were prepared in the same manner as in Example 1 provided that hyaluronic acid instead of ubiquinone 10 was used in the ingredients of Example 1.

EXPERIMENT

Experiment 1

Water Retention Effect in Skin

By using 4 volunteers (water content of cheeks was 40–50%), sheet-like packs were applied on their cheeks, and after 15 minutes the packs were taken off (released) and change of water content was measured with the passage of time.

The results are shown in FIG. 1.

In case of the pack of Comparative example 1, water content of the skin at 10 minutes later after taking the packs off was high, but with the passage of time, water content in the skin decreased.

On the other hand in case of Example 1, water content of the skin at 10 minutes later after taking off the packs was lower than the water content in case of Comparative example 1, but higher water content than water content before application of the pack was kept for longer hours. Namely, the sheet-like pack of the present invention shows the excellent preparation in the point of water retention in skin.

Experiment 2

Prevention Effect on Small Wrinkles by Sheet-Like Packs Containing Ubiquinone 10

Sheet-like packs (Examples 2 and 4, Comparative examples 2 and 3) were tested on 10 female volunteers taking care of small wrinkles and prevention or improvement effect of small wrinkles was observed. Each pack of Examples 2 and 4, Comparative examples 2 and 3 was applied to the region of said small wrinkles overnight once a day and after a week, efficacy (improvement) was evaluated based on each evaluation item (small wrinkles on skin, gloss of skin, tension of skin, and wetness of skin) along with following standards.

Standards
+: Improvement was observed.
±: Slightly improvement was observed.
−: Improvement was not observed.
The results are shown in Table 4.

TABLE 4

| Item | Standard | Ex. 2 | Ex. 4 | Comp. Ex. 2 | Comp. Ex. 3 |
|---|---|---|---|---|---|
| Small wrinkles | + | 9 | 10 | 3 | 6 |
|  | ± | 1 | 0 | 3 | 3 |
|  | − | 0 | 0 | 4 | 1 |
| Gloss | + | 9 | 10 | 5 | 7 |
|  | ± | 1 | 0 | 2 | 2 |
|  | − | 0 | 0 | 3 | 1 |
| Tension | + | 9 | 9 | 7 | 7 |
|  | ± | 1 | 1 | 2 | 3 |
|  | − | 0 | 0 | 1 | 0 |
| Wetness | + | 10 | 10 | 9 | 10 |
|  | ± | 0 | 0 | 1 | 0 |
|  | − | 0 | 0 | 0 | 0 |

Each number in the above table means number of people who expressed the said standard on each item.

The sheet-like packs containing Ubiquinone 10 of Examples 2 and 4 showed far superior improvement and prevention efficacy on small wrinkles compared to the pack of Comparative example 2 and showed superior effect to the pack containing hyaluronic acid (Comparative example 3).

Figure 1:
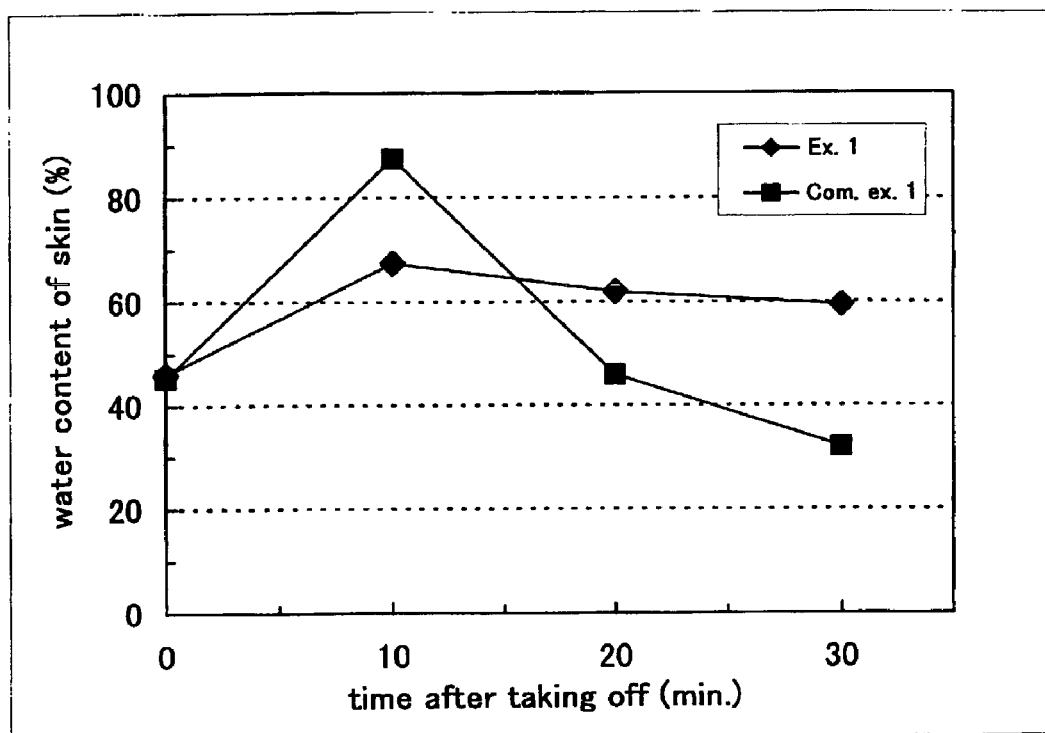
FIG. 1 shows effect of the sheet-like packs in regard to water content.

The invention claimed is:
1. A sheet-like pack composition comprising:
   a mixture of water soluble high molecular weight compounds consisting of a polyacrylic acid, a polyacrylic acid salt and sodium carboxymethyl cellulose, or con- sisting of gelatin, a polyacrylic acid, a polyacrylic acid salt and sodium carboxymethyl cellulose, water and ubiquinone 10 as an active ingredient, which are contained in a base;

wherein the content of ubiquinone 10 per total amount of the base is 0.001–5% by weight, the content of the mixture of the water soluble high molecular weight compounds per total amount of the base is 3–20% by weight, and the content of the water per total amount of the base is 50–70% by weight.

2. The sheet-like pack of claim 1, wherein the content of ubiquinone 10 per total of amount of the base is 0.02–2% by weight.

3. The sheet-like pack of claim 1, wherein the amount of the mixture of the water-soluble high molecular weight compounds is about 7% to about 14% by weight.

4. A method of treating small wrinkles, said method comprising applying the sheet-like pack of claim 1 to the skin of a human face.

5. The sheet-like pack of claim 1, wherein amount of the mixture of the water soluble high molecular weight compounds per total amount of the base is 7.8–13.25% by weight.

6. The sheet-like pack of claim 1, wherein the mixture of the water soluble high molecular weight compounds consist of polyacrylic acid, polyacrylic acid salt and sodium carboxymethyl cellulose.

7. The sheet-like pack of claim 1, wherein the mixture of the water soluble high molecular weight compounds consist of polyacrylic acid, polyacrylic acid salt, sodium carboxymethyl cellulose and gelatin.

8. The sheet-like pack of claim 1, wherein the content of ubiquinone 10 per total amount of the base is 0.002–2% by weight.

9. The sheet-like pack of claim 1, wherein the amount of the mixture of the water soluble high molecular weight compounds per total amount of the base is 3–13.25% by weight.

10. The sheet-like pack of claim 1, wherein the content of the mixture of the water soluble high molecular weight compounds per total amount of the base is 7.8–20% by weight.

11. A method for treating small wrinkles, said method comprising applying the sheet-like pack of claim 7 or 8 to the skin of a human face.

12. The sheet-like pack of claim 1, further comprising a wetting agent.

13. The sheet-like pack of claim 12, wherein said wetting agent is selected from the group consisting of glycerin, sorbitol, propylene glycol, 1,3-butylene glycol, and polyethylene glycol.

* * * * *